(12) United States Patent
Metcalf et al.

(10) Patent No.: US 6,193,962 B1
(45) Date of Patent: Feb. 27, 2001

(54) PHARMACEUTICAL FORMULATION COMPRISING A 2-AMINOACETAMIDE DERIVATIVE AND AN ION EXCHANGE RESIN

(75) Inventors: Stephen Metcalf, Loughborough; Keith Purdy, Radcliffe, both of (GB)

(73) Assignee: AstraZeneca UK Limited, London (GB)

( * ) Notice: Subject to any disclaimer, the term of this patent is extended or adjusted under 35 U.S.C. 154(b) by 0 days.

(21) Appl. No.: 09/180,134

(22) PCT Filed: Jul. 17, 1998

(86) PCT No.: PCT/SE98/01398

§ 371 Date: Nov. 3, 1998

§ 102(e) Date: Nov. 3, 1998

(87) PCT Pub. No.: WO99/04779

PCT Pub. Date: Feb. 4, 1999

(30) Foreign Application Priority Data

Jul. 24, 1997 (SE) .................................................. 9702793

(51) Int. Cl.[7] .................................................. A61K 47/32
(52) U.S. Cl. ........................................ 424/78.12; 514/974
(58) Field of Search ........................... 424/78.12; 514/974

(56) References Cited

U.S. PATENT DOCUMENTS

| | | | |
|---|---|---|---|
| 3,100,738 | * | 8/1963 | Cavallito ............................ 424/78.12 |
| 4,714,620 | | 12/1987 | Bunick et al. . |
| 5,334,378 | * | 8/1994 | Mitani et al. ...................... 424/78.12 |
| 5,626,879 | | 5/1997 | Anaebonam et al. . |
| 5,643,560 | * | 7/1997 | Bergwitz-Larsen et al. ..... 424/78.12 |

FOREIGN PATENT DOCUMENTS

| | | |
|---|---|---|
| 0 279 937 | 8/1988 | (EP) . |
| 0 279 937 A1 | 8/1988 | (EP) . |
| 0 427 427 A2 | 5/1991 | (EP) . |
| 0 435 684 A1 | 7/1991 | (EP) . |
| 0 501 763 A1 | 9/1992 | (EP) . |
| 0 564 154 A1 | 10/1993 | (EP) . |
| 2 676 364 | 11/1992 | (FR) . |
| 857194 | * 12/1960 | (GB) . |

* cited by examiner

Primary Examiner—Peter F. Kulkosky
(74) Attorney, Agent, or Firm—Nixon & Vanderhye

(57) ABSTRACT

The invention relates to novel formulations comprising a medicament and an ion-exchange resin.

13 Claims, No Drawings

PHARMACEUTICAL FORMULATION COMPRISING A 2-AMINOACETAMIDE DERIVATIVE AND AN ION EXCHANGE RESIN

The present invention relates to novel formulations, in particular a formulation comprising an anticonvulsant and an ion-exchange resin.

European Patent Application No. 279937 describes a group of compounds which are NMDA antagonists and are indicated as anticonvulsants. EPA 279937 discloses the compound 2-amino-N-(1,2-diphenyl-1-methylethyl) acetamide hydrochloride (which has the INN remacemide hydrochloride). This compound is useful for the treatment of, inter alia, epilepsy, Parkinson's disease and Huntingdons disease.

Conventional liquid formulations of the above compound have a bitter and unpleasant taste which is a particular disadvantage for paediatric administration. Therefore there is a need for formulations containing remacemide which overcome this problem. Pharmaceutical formulations comprising a vasodilator in combination with an ion-exchange resins are known in the art, for example from EPA 501 763. There is no mention of other medicaments in combination with an ion-exchange resin. It has now surprisingly been found that if remacemide is combined with an ion-exchange resin the bitter taste of the resulting formulation is substantially eliminated. In addition to having a pleasant taste and mouthfeel, the formulations of the invention show good bioavailability.

In a first aspect the present invention therefore provides formulation comprising a compound of formula (I) or a salt thereof:

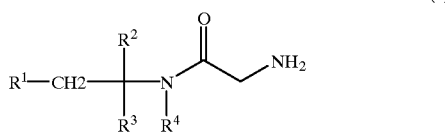

(1)

where:

$R^1$ and $R^2$ are independently phenyl or 4fluorophenyl;

$R^3$ is hydrogen, $C_{1-6}$ alkyl or methoxycarbonyl;

$R^4$ is hydrogen or methyl; in association with an ion-exchange resin and optionally further pharmaceutically acceptable carriers or excipients.

The preferred compound of formula (I) is 2-amino-N-(1,2-diphenyl-1-methylethyl)acetamide (remacemide) or a salt thereof, preferably the hydrochloride salt.

Examples of suitable ion exchange resins include acidic low cross-linked carboxylic acid resins prepared from methacrylic acid and divinyl benzene such as Amberlite IRP 64, IRP 69 and IRP 88. Preferably the ion exchange resin is Amberlite IRP64, Amberlite IRP-88, Purolite C115 KMR or Purolite C115 HMR. More preferably the ion exchange resin is Amberlite IRP-64 or Purolite C115 HMR, most preferably Amberlite IRP64. In the acidic conditions of the stomach the resin becomes fully un-ionised resulting in rapid release of the compound of formula (I). Preferably the level of resin present in the final suspension is about 3.0% w/v for a remacemide concentration of about 10 mg/ml, and about 6.0% w/v for a remacemide concentration of about 20 mg/ml.

In a further aspect the invention provides a compound of formula (I), in particular remacemide or a salt thereof, in the form of a complex with an ion exchange resin.

The formulations of the invention can be in the form of a suspension or a reconstitutable formulation suitable for reconstitution with a convenient volume of water or other palatable aqueous medium.

The viscosity of permanent suspensions of the invention can be increased by the addition of one or more hydrophillic polymers (viscosifiers). The addition of such polymers facilitates administration by improving mouthfeel and maintaining the suspension after shaking which ensures homogeneity and dose reproducibility. Preferred polymers are those that provide the desired rheological properties and give a good mouthfeel, including xanthan gum and microcrystalline cellulose/sodium carboxymethyl cellulose (Avicel). Additionally a protective colloid can be included in the formulation, for example xanthan gum, carboxymethyl cellulose or Methocel 90HG (hydroxypropylmethylcellulose). Preferably the colloid is added at about 15–20% of the hydrophillic polymer.

The suspensions of the invention can also contain a flocculant to prevent the resin forming a sediment which is non-redispersible. Preferred flocculants include cationic polymeric materials such as chitosan (Protosan).

Preferably the formulations of the invention are in the form of a reconstitutable formulation. The formulations of the invention are preferably supplied in dry powder form in individual bottles for reconstitution by the pharmacist.

Reconstitutable formlations of the invention can also contain viscosifiers as described above. Particularly suitable viscosifiers include Avicel and Keltrol.

If desired the resin can be milled to a selected the mean particle size, using, for example, centrifugal ball milling. However one advantage of the formulations of the invention is that milling of the resin is unecessary if the formulations contains an agent to improve mouthfeel, that is to say, eliminate the gritty texture of the resinate. If the need for milling is eliminated this is highly advantageous, since the resin can be difficult to mill on a large scale, and milling tends to increase methacrylic acid monomer levels in the case of Amberlite resin which is not desirable from a safety viewpoint. Suitable agents which improve mouthfeel include polyvinylpyrrolidine, in particular Kollidon 90F. The mouthfeel enhancer can be present in the range of about 0.1 to about 10% w/v, preferably about 1% to about 6% with a preferred maximum of about 2% for a paediatric formulation.

In a further aspect the invention therefore provides a pharmaceutical formulation comprising polyvinylpyrrolidine whereby the polyvinylpyrrolidine reduces the grittiness of the suspended particles enhancing palatability of the formulation.

The formulations of the invention can contain other pharmaceutically acceptable carriers or excipients.

Preservatives can be added to the formulations of the invention. Any preservative compatible with the formulation is suitable. Preferred preservatives include esters of hydroxybenzoic acid, in particular the commercial blend of methyl, ethyl and propyl esters known as Niasept. Niasept sodium is desirable for reconstitutable formulations since it is preferable that the formulation is cold water soluble.

The formulations of the invention can contain one or more flavourings. The flavouring substance may be any edible flavouring substance which is acceptable and approved for use with pharmaceutical formulations. Very many such substances are known. The flavouring substance may for example be a natural or artificial flavouring, such as of a fruit, vegetable or confectionery taste. Additionally or alternatively the flavouring substance may comprise a sweetener, such as sugar, or an artificial sweetner such as sodium saccharin or aspartame. In the case of paediatric formulations an artificial sweetner is preferred.

The formulations of the invention are suitable for the treatment or prophylaxis of disease conditions where administration of an NMDA antagonist is beneficial. Such conditions are listed in EPA 279937, EPA 356035, EPA 427 427, EPA 637956 and EPA 648489. In a further aspect the invention therefore provides a formulation as defined herein for use in therapy, and particularly for the treatment and prophylaxis of epilepsy, Parkinson's disease and Huntingdons disease. Preferably the formulations of the invention are used for the treatment and prophylaxis of epilepsy. As mentioned above, the reconstitutable formulations of the invention are particularly suitable for paediatric administration.

The invention also provides a formulation as defined herein for the treatment or prophylaxis of epilepsy. Suitable daily dose ranges are from about 1.0 mg/kg to about 50 mg/kg. Unit doses may be administered once or more than once a day, for example, 2, 3, or 4 times a day, more usually 1 or 2 times a day.

The invention is illustrated by the following examples.

EXAMPLE 1

Suspension Formulation

| Material | Concentration % w/w |
| --- | --- |
| remacemide HCl | 1.00 (as base) |
| Amberlite IRP64 | 3.00 |
| Nipasept | 0.25 |
| Avicel | 2.50 |
| Sodium hydroxide | qs |
| Water | to 100 % |

Flavourings, artifical sweetners, colourings etc can also be added as appropriate.

The formulation can be prepared as follows:
1. Mill the Amberlite resin (400 g) using a centrifugal ball mill to achieve a median particle size of 18 µm.
2. Prepare Avicel suspension by gradually adding 250 g of Avicel to 3000 ml water with stirring.
3. In a separate vessel heat 5000 ml water to 90° C. and add 25 g Niasept with stirring.
4. Allow to cool to below 40° C. and add 140 g remacemide HCl with stirring.
5. Add 300 g Amberlite IRP64, adjust pH to 6 and allow to stir overnight.
6. Readjust the PH to 6 and add the Avicel dispersion with stirring
7. When homogeneous, fill into bottles and cap.

EXAMPLE 2

Reconstitutable Formulation

For incorporation into a reconstitutable formulation, a dried remacemide resinate complex is prepared.

The required quantity of resin is added to a solution of remacemide HC1 and stirred for several hours at about pH 6, to allow maximal drug binding to the resin. The solids are then isolated by either centrifugation or filtration, and then washed with water to remove unbound drug, which would impart a bitter taste in the formulation on reconstitution. The remacemide resinate is then dried, typically at 60–80° C. and passed through a seive to break up agglomerates. Typically drug levels are 200–300 mg remacemnide per gram of dried remacemide resinate.

The formulation details for the reconstituted product (20 mg/ml) are as follows:

| Ingredient | % w/w | % w/w | Purpose |
| --- | --- | --- | --- |
| | Formula 1 | Formula 2 | |
| Remacemide | 2 | 2 | Active |
| Resin | 6 | 6 | Taste mask |
| Avicel CL-611 | 1.6 | — | Viscosifier |
| Keltrol RD | — | 0.5 | Viscosifier |
| Kollidon 90F | 6 | 6 | Improve mouthfeel |
| Nipasept Na | 0.2 | 0.2 | Preservative |
| Water | to 100 | to 100 | Vehicle |
| | Formula 3 | Formula 4 | |
| Remacemide | 2 | 2 | Active |
| Resin | 6 | 6 | Taste mask |
| Avicel CL-611 | 1.8 | — | Viscosifier |
| Keltrol RD | — | 0.6 | Viscosifier |
| Kollidon 90F | 2 | 2 | Improve mouthfeel |
| Nipasept Na | 0.2 | 0.2 | Preservative |
| Water | to 100 | to 100 | Vehicle |

What is claimed is:

1. A pharmaceutical formulation comprising an effective amount of a compound of formula (I) or a salt thereof:

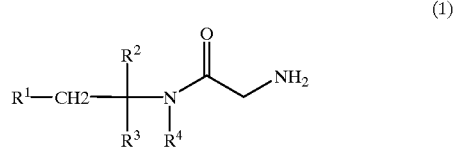

(1)

where:
$R^1$ and $R^2$ are independently phenyl or 4-fluorophenyl;
$R^3$ is hydrogen, $C_{1-6}$ alkyl or methyoxycarbonyl;
$R^4$ is hydrogen or methyl;
in association with a taste masking effective amount of an ion exchange resin prepared from methacrylic acid and divinyl benzene;
and optionally further pharmaceutically acceptable carriers or excipients.

2. A formulation according to claim 1 in which the compound of formula (I) is 2-amino-N-(1,2-diphenyl-1-methylethyl)acetamide or a salt thereof.

3. A formulation according to claim 1 in which the ion exchange resin is an acidic low cross-linked carboxylic acid resin.

4. A formulation according to claim 1 which further contains one or more hydrophillic polymers.

5. A formulation according to claim 1 which further contains a protective colloid.

6. A formulation according to claim 1 which further contains a preservative.

7. A formulation according to claim 1 which further contains an agent selected from the group consisting of a flavoring and a sweetener.

8. A formulation according to claim 1 in the form of a suspension.

9. A formulation according to claim 1 in reconstitutable form.

10. A compound of formula (I) as defined in claim 1 in the form of a complex with a taste-masking effective amount of an ion-exchange resin prepared from methacrylic acid and divinyl benzene.

11. A complex according to claim 10 wherein the compound of formula (I) is remacemide or a salt thereof.

12. A process for preparing a formulation as claimed in claim 1 which comprises admixing a compound of formula (I) or a salt thereof with an ion-exchange resin prepared from methacrylic acid and divinyl benzene and optionally further pharmaceutically acceptable carriers or excipients.

13. A method of treatment or prophylaxis of epilepsy, Parkinson's disease or Huntington's disease in a patient in need of such treatment, said method comprising the step of administering to said patient a therapeutically effective amount of a formulation according to claim 1.

* * * * *